United States Patent [19]

Tadanier et al.

[11] 4,269,970
[45] May 26, 1981

[54] 1,2-CARBAMATES OF FORTIMICIN B AND DERIVATIVES

[75] Inventors: John S. Tadanier; Jerry R. Martin, both of Waukegan, Ill.

[73] Assignee: Abbott Laboratories, North Chicago, Ill.

[21] Appl. No.: 79,138

[22] Filed: Sep. 26, 1979

[51] Int. Cl.³ .................... C07H 15/22; C07D 413/02
[52] U.S. Cl. .................................. 536/17 R; 548/221; 424/180
[58] Field of Search ........................ 548/221; 424/180; 536/17 R, 17 B

[56] References Cited

U.S. PATENT DOCUMENTS

| | | | |
|---|---|---|---|
| 4,065,616 | 12/1977 | Umezawa et al. | 536/18 |
| 4,091,032 | 5/1978 | Tadanier et al. | 424/118 |
| 4,169,942 | 10/1979 | Mochda et al. | 424/180 |
| 4,176,178 | 11/1979 | Martin et al. | 424/180 |

OTHER PUBLICATIONS

Umezawa et al., Bulletin of Chemical Society of Japan, vol. 44, pp. 1411–1415, (1971).

*Primary Examiner*—Mary C. Lee

*Attorney, Agent, or Firm*—Joyce R. Niblack; Gildo E. Fato; Robert L. Niblack

[57] ABSTRACT

A 1,2-carbamate of fortimicin B and derivatives represented by the formula:

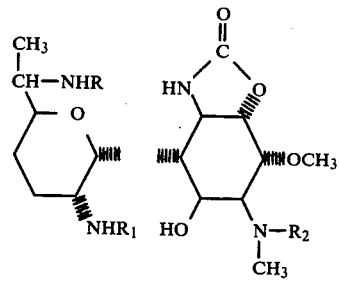

wherein: R is hydrogen or monocyclicaryloxycarbonyl, $R_1$ is hydrogen or monocyclicaryloxycarbonyl; and $R_2$ is selected from the group consisting of loweralkyl, loweralkoxycarbonyl aminoloweralkyl, hydroxyloweralkyl, hydroxy-substituted aminoloweralkyl, an amino acid residue, and N-protected amino acid residue, or when R and $R_1$ are hydrogen, $R_2$ can also be hydrogen; and the acid addition salts thereof when R,$R_1$ or $R_2$ are hydrogen or an unprotected aminoacid residue.

13 Claims, No Drawings

1,2-CARBAMATES OF FORTIMICIN B AND DERIVATIVES

BACKGROUND OF THE INVENTION

Aminoglycoside antibiotics are a useful class of antibiotics which include streptomycins, neomycins, kanamycins, gentamicins, tobramycins, amikacin and the more recently discovered fortimicins. It is known that chemical modification of the aminoglycoside antibiotics can result in altered antibacterial and pharmacological properties of the aminoglycosides. For example, certain modifications in the gentamicin and kanamycin family of antibiotics provide compounds which are less toxic than the parent antibiotics. Further, certain modifications in the gentamicin and kanamycin series have been found to alter the antibacterial spectra advantageously either by increasing the intrinsic activity or increasing the activity against resistant strains.

While the fortimicins are a relatively new family of antibiotics, chemical modification have been found to advantageously modify the properties of these antibiotics as well. One such modification has provided a series of 2-deoxyfortimicins, specifically, 2-deoxyfortimin B which is an intermediate for producing the antibiotic 2-deoxyfortimicin A and 2-deoxyfortimicin B derivatives. These compounds are disclosed in commonly assigned, co-pending allowed patent application U.S. Ser. Nos. 863,006 now U.S. Pat. Nos. 4,192,867 and 863,009, now U.S. Pat. No. 4,169,198 both filed on Dec. 21, 1977.

The present invention provides 1,2-carbamates of fortimicin B which are intermediates for the preparation of the corresponding 1,5-carbamates, disclosed in allowed co-pending application Ser. No. 079,133, filed of even date with the present, commonly assigned application. The 1,5-carbamates are useful as intermediates in the preparation of 2-deoxyfortimicins.

Two additional fortimicin B-1,2-carbamates are disclosed in our commonly assigned, co-pending application Ser. No. 079,144, filed of even date herewith.

SUMMARY OF THE INVENTION

The present invention provides a series of 1,2-carbamates of fortimicin B. The compounds are useful as intermediates in the preparation of the corresponding 1,5-carbamates, which are useful as intermediates in the preparation of 2-deoxyfortimicins.

DETAILED DESCRIPTION OF PREFERRED EMBODIMENTS

The 1,2-carbamates of fortimicin B of this invention are represented by the formula:

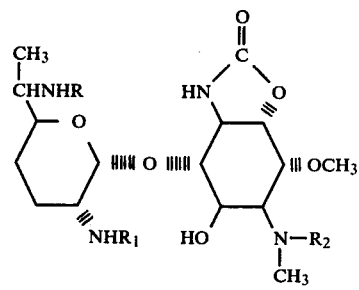

wherein: R is hydrogen or monocyclicaryloxycarbonyl; $R_1$ is hydrogen or monocyclicaryloxycarbonyl; and $R_2$ is selected from the group consisting of loweralkyl, lower aminoloweralkyl, hydroxyloweralkyl, hydroxy-substituted aminoloweralkyl, an amino acid residue, an N-protected amino acid residue, and when R and $R_1$ are hydrogen, $R_2$ can also be hydrogen, and when one of more R, $R_1$ and $R_2$ are hydrogen, the acid addition salts thereof.

The term "moncyclicaryloxycarbonyl", as used herein, refers to the amine-protecting groups commonly used such as benzyloxycarbonyl, 2-bromobenzyloxycarbonyl, etc.

The term "loweralkyl" refers to straight and branched chain alkyl radicals having from one to six carbon atoms such as methyl, ethyl, n-propyl, iso-propyl, n-butyl, n-hexyl, etc.

The term "loweralkoxycarbonyl" refers to groups containing alkoxy radicals having from 1–6 carbon atoms, i.e. methoxycarbonyl, ethoxycarbonyl, etc.

The term "an amino acid residue" refers to naturally occurring amino acid residues such as glycyl, alanyl, sarcosyl, valyl, threonyl, leucyl, etc., either in the D,L or DL configurations.

The term "acid addition salts" refers to salts such as the hydrochloride, hydrobromide, sulfate, oleate, valerate, etc.

The preparation of the compounds of this invention is set forth generally in the following reaction schemes and in detail in the following examples.

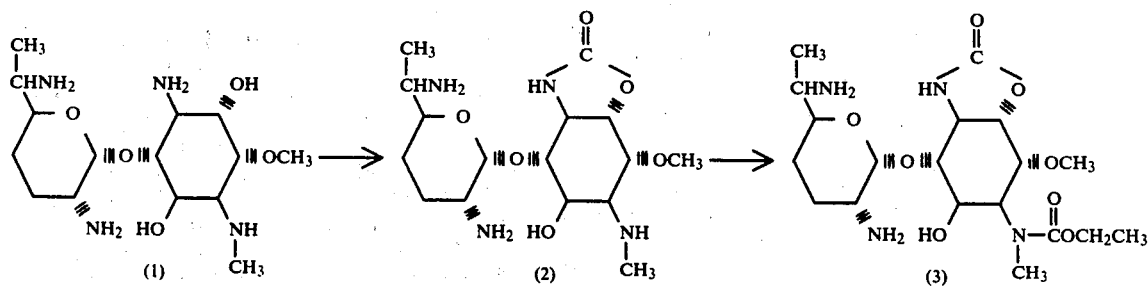

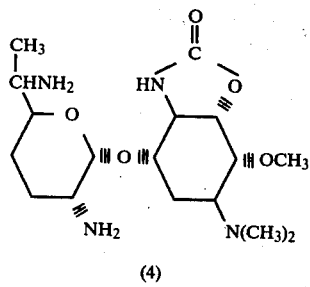 (4)
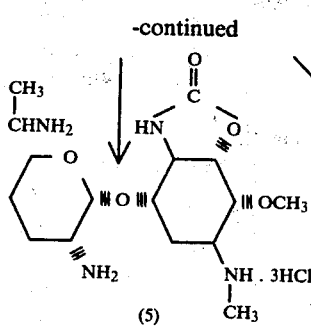 (5)
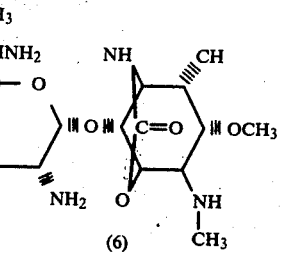 (6)

The following examples further illustrate the present invention.

EXAMPLE 1

1,2',6'-Tri-N-benzyloxycarbonylfortimicin B(1)

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° C. for 3 hours and then at room temperature for 22 hours. The major portion of the methanol is evaporated under reduce pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-concentrated ammonium hydroxide[23.4:4.1:0.1(v/v/v)] gives 1.05 g of 1,2',6'-tri-N-benzyloxycarbonylfortimicin B:$[\alpha]_D^{25}+16.5°$(c 1.0,$CH_3OH$);IR($CDCl_3$)1712 and 1507 $cm^{-1}$;NMR($CDCl_3$)$\delta$ 1.03($C_6'$—$CH_3$,$J_{6',7'}=6.0$ Hz),2.32($C_4$—$NCH_3$), 3.41($OCH_3$).

EXAMPLE 2

2',6'-Di-N-benzyloxycarbonylfortimicin B-1,2-carbamate(4)

To a magnetically stirred solution of 8.15 g of 1,2',6'-tri-N-benzyloxycarbonylfortimicin B-4,5-formaldehydeoxazolidine(2) in 160 ml of N,N-dimethylformamide under an atmosphere of nitrogen, cooled in an ice bath, is added 2.32 g of a 57% oily dispersion of sodium hydride. The resulting suspension is kept in the ice bath for 1 hour and then kept at room temperature for 21 hours. To the resulting solution, cooled in an ice bath, is cautiously added a solution prepared from 10 ml of acetic acid and 20 ml of water. The resulting solution is shaken with a mixture of 400 ml of chloroform, 800 ml of 5% aqueous sodium bicarbonate solution. The chloroform solution is separated and washed with 800 ml of 5% aqueous sodium chloride solution. The aqueous solutions are washed in series with four 200 ml portions of chloroform. The chloroform solutions are combined and dried over magnesium sulfate. The chloroform is evaporated under reduced pressure, and residual N,N-dimethylformamide is removed by co-distillation with toluene under reduced pressure leaving 7.86 g of crude 2',6'-di-N-benzyloxycarbonylfortimicin B-1,2-carbamate-4,5-formaldehyde oxazolidine(3). A solution of 7.81 g of the latter, 2.64 g of hydroxylamine hydrochloride, 7.35 ml of acetic acid and 456 ml of methanol is heated under reflux for 1 hour. The major portion of the methanol is evaporated under reduced pressure, and the residue is shaken with a mixture of 400 ml of 1:1(v/v) concentrated ammonium hydroxide-water and 200 ml of chloroform. The chloroform solution is separated and washed with 400 ml of 5% aqueous sodium chloride. The aqueous solutions are washed in series with four 200 ml portions of chloroform. The chloroform solutions are combined and dried over magnesium sulfate. Evaporation of the chloroform under reduced pressure leaves 7.72 g of crude product(4). Chromatography of 1.01 g of the latter on a column of 100 g of silica gel, packed and eluted with a solvent system prepared from 1,2-dichloroethane-isopropanol[18.5:1.5(v/v)] yields 0.539 g of pure product :$[\alpha]_D^{21}+27°$(c 1%,$CH_3OH$);NMR ($CDCl_3$)$\delta$ 1.14 d(J=6.5 Hz)($C_6'$—$CH_3$);2.39($NCH_3$);3.45($OCH_3$); IR($CDCl_3$) 3439,3411,3353,1765,1705 $cm^{-1}$.

Analysis Calcd. for $C_{32}H_{43}N_4O_{10}$: C,59.70; H,6.73; N,8.70. Found: C,59.56; H,6.68; N,8.65.

EXAMPLE 3

4-N-Ethoxycarbonyl-2',6'-di-N-benzyloxycarbonylfortimicin B 1,2-carbamate

To a magnetically stirred suspension of 0.750 g of 2',6'-di-N-benzyloxycarbonylfortimicin B-1,2-carbamate, 37 ml of methanol, and 18.5 ml of a solution prepared from 3.0 g of sodium bicarbonate in 72 ml of water is added 0.28 ml of ethyl chloroformate. After one hour, an additional 0.3 ml of ethyl chloroformate is added and stirring is continued for 4 hours. The resulting solution is shaken with a mixture of 200 ml of chloroform and 200 ml of water. The aqueous solutions are washed in series with three 100 ml portions of chloroform. The chloroform solutions are combined and dried over magnesium sulfate. Evaporation of the chloroform left 0.789 g of product: NMR($CDCl_3$)$\delta$ 1.15d(J=6.8 Hz)($C_6'$—$CH_3$), 1.25 t(J=6.65 Hz)($OCH_2\underline{CH}_3$). 2.96($NCH_3$), 3.48($OCH_3$).

EXAMPLE 4

4-N-Methyl-2',6'-di-N-benzyloxycarbonylfortimicin B-1,2-carbamate

To a magnetically stirred solution of 1.01 g of 4-N-methyl-1,2',6'-tri-N-benzyloxyfortimicin B, prepared according to U.S. Pat. No. 4,091,032, in 20 ml of dry N,N-dimethylformamide, cooled in an ice bath, under a nitrogen atmosphere, is added 0.02843 g of a 57% oily dispersion of sodium hydride. Stirring is continued fo 0° C. for one hour. The ice bath is removed and the reaction mixture is kept at ambient temperature for 22 hours during which time a gel forms. A solution of 0.8 ml of acetic acid in 2 ml of water is added to the cooled gel, and the resulting mixture is shaken with a mixture of 100 ml of chloroform and 200 ml of 5% aqueous sodium bicarbonate. The chloroform solution is separated and washed with 200 ml of water. The aqueous solutions are washed in series with three 100 ml portions of chloroform. The chloroform solutions are combined and the chloroform is evaporated under reduced pressure. Residual N,N-dimethylformamide is removed by co-distillation with toluene under reduced pressure to yield 0.930 g of crude product. Chromatography of the latter on a column of 80 g of silica gel packed and eluted with a solvent system composed of 1,2-dichloroethane-methanol-concentrated ammonium hydroxide[23.4:1.4:0.1(v/v/v)] gives 0.384 g of pure product:NMR(CDCl$_3$) 1.17 d(J=7.2 Hz)(C$_6'$—CH$_3$), 2.46(N(CH$_3$)$_2$), 3.47(OCH$_3$); IR(CDCl$_3$) 3443,3313, 1765, 1713 cm$^{-1}$.

EXAMPLE 5

Fortimicin B-1,2-carbamate trihydrochloride

2',6'-Di-N-benzyloxycarbonylfortimicin B-1,2-carbamate(810 mg), prepared according to the method of Example 6, in 75 ml of 0.2 N hydrochloric acid in methanol is hydrogenated under 3 atmospheres of hydrogen for 4 hr. in the presence of 810 mg of 5% palladium on carbon. The catalyst is removed by filtration and the methanol is evaporated under reduced pressure. Residual hydrochloric acid is removed by co-distillation with methanol under reduced pressure leaving 619 mg of product as a glass: $[\alpha]_D^{22}$+43°(c 1%,CH$_3$OH); NMR(D$_2$O)$\delta$ 1.86d (J=7.0 Hz)(C$_6'$—CH$_3$),3.38(NCH$_3$), 4.08(OCH$_3$), 6.40d (J=3.7 Hz)(C$_1'$—H),IR(KBr) 1750 cm$^{-1}$.

EXAMPLE 6

2',6'-Di-N-benzyloxycarbonylfortimicin B-1,5-carbamate

A solution of 7.22 g of crude 2',6'-di-N-benzyloxycarbonylfortimicin B-1,2-carbamate(4), prepared as described above, 360 ml of methanol and 180 ml of 1:4(v/v) concentrated ammonium hydroxide-water is kept at room temperature for two days. The major portion of the methanol is evaporated under reduced pressure, and the residue is shaken with a mixture of 300 ml of chloroform and 400 ml of 5% aqueous sodium bicarbonate. The chloroform solution is separated and washed with 400 ml of water. The aqueous solutions are washed in series with three 200 ml portions of chloroform. The chloroform solutions are combined and the chloroform is evaporated under reduced pressure leaving 7.0 g of light orange glass. Chromatography of the latter on a column of 450 g of silica gel packed and eluted with a solvent system composed of methylene chloride-methanol-concentrated ammonium hydroxide[20:2:0.1(v/v/v)] gives 3.26 g of pure 2',6'-di-N-benzyloxycarbonylfortimicin B-1,5-carbamate:- $[\alpha]_D^{23}$+101° (c 1%,CH$_3$OH),NMR(CDCl$_3$) $\delta$ 1.14 d(J=3 Hz)(C$_6'$—CH$_3$), 2.36(NHCH$_3$), 3.45(OCH$_3$),IR(CDCl$_3$) 3529,3439,3324,1712 cm$^{-1}$.

Analysis Calcd. for C$_{32}$H$_{42}$N$_4$O$_{10}$: C,59.80; H,6.59; N,8.72. Found: C,59.43; H,6.72; N,8.63.

The following reaction scheme summarized the preparation of 2-deoxyfortimicin B from the 1,5-carbamate of Example 6.

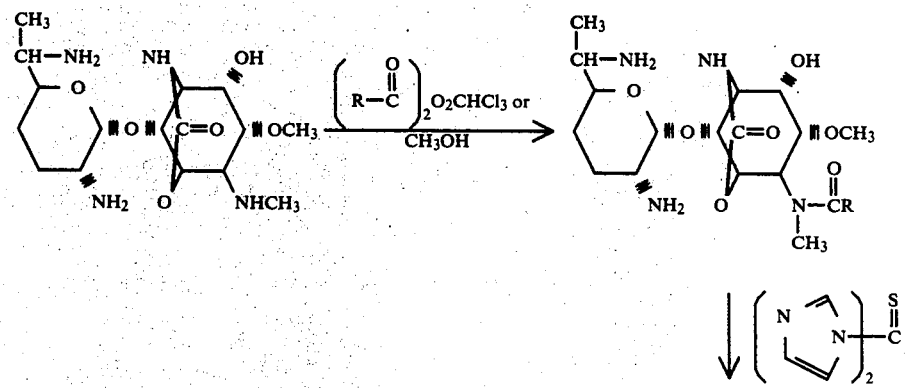

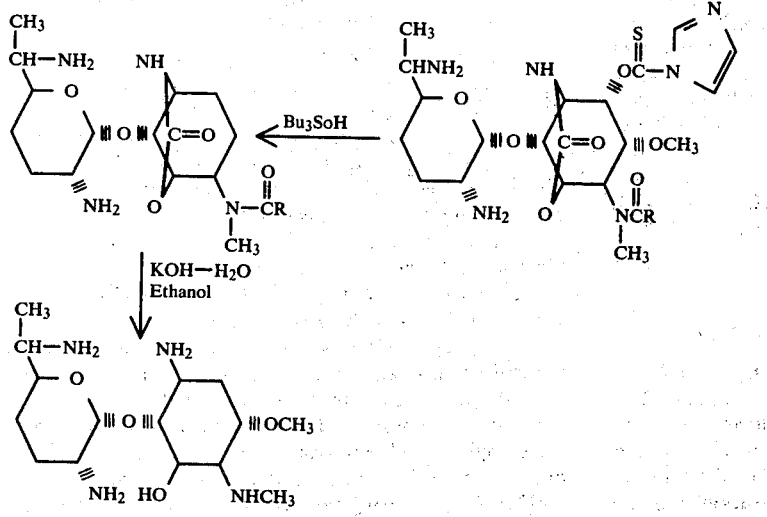
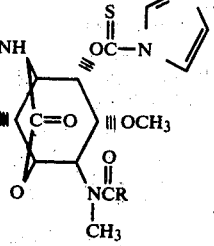

2-Deoxyfortimicin A can be prepared in turn from 2-deoxyfortimicin B according to the teachings of U.S. Pat. No. 4,192,867, issued Mar. 11, 1980 from U.S. Ser. No. 863,006 and according to the methods of Examples 8 and 9.

EXAMPLE 7

Tetra-N-benzyloxycarbonyl-2-deoxyfortimicin A

A stirring solution of 0.807 g of 1,2',6'-tri-N-benzyloxycarbonyl-2-deoxyfortimicin B in 14 ml of dry tetrahydrofuran is treated for 18 hours with 0.439 g of the N-hydroxysuccinimide ester of N-benzyloxycarbonylglycine. The tetrahydrofuran is evaporated under reduced pressure to give 1.231 g of colorless froth. The froth is chromatographed on a column (2.0×44 cm) of silica gel prepared and eluted with a solvent system consisting of benzene-methanol-95% ethanol-concentrated ammonium hydroxide [23,5:1.5:1.9:0.2(v/v/v)]. Fractions containing tetra-N-benzyloxycarbonyl-2-deoxyfortimicin A are taken to dryness under reduced pressure and rechromatographed on a column of Sephadex LH-20 prepared and eluted with 95% ethanol. Elutes containing the major product are evaporated to give 0.623 g of tetra-N-benzyloxycarbonyl-2-deoxyfortimicin A.

EXAMPLE 8

2-Deoxyfortimicin A tetrahydrochloride

A solution of 0.463 g of the above intermediate in 60 ml of 0.2 N hydrochloric acid in methanol is treated for 4 hours with 0.463 g of 5% palladium on carbon under 3 atmospheres of hydrogen. The catalyst is collected on a filter and washed with several mall portions of methanol. the filtrate is evaporated to dryness under reduced pressure to give a white solid. Excess hydrochloric acid is removed by repeated co-distillation with methanol to leave 0.305 g of product.

EXAMPLE 9

4-N-Methylfortimicin B-1,2-carbamate trihydrochloride

The benzyloxycarbonyl groups of 4-N-methyl-2',6'-di-N-benzyloxycarbonylfortimicin B-1,2-carbamate are removed by catalytic hydrogenation according to the procedure of Example 5 to give 4-N-methylfortimicin B-1,2-carbamate trihydrochloride.

It will be apparent to one of ordinary skill in the art that other 4-N-fortimicin B-1,2-carbamates can be readily prepared by starting with the appropriate 4-N-substituted-tri-N-protected fortimicin B derivative following the procedures set forth herein.

The desired 2-deoxyfortimicin B derivative can be readily obtained from the fortimicin B-1,2-carbamates of this invention by conversion first to the corresponding 1,5-carbamate as disclosed in detail in commonly assigned, co-pending application Ser. No. 079,133, filed of even date herewith, and reacting the appropriate 1,5-carbamate according to the procedure described by Barton et al., *J. Chem. Soc.*, Perkin I, 1574 (1974).

EXAMPLE 10

1,2',6'-Tri-N-benzyloxycarbonylfortimicin B-4,5-formaldehyde oxazolidine

A solution of 16.0 g of 1,2',6'-tri-N-benzyloxycarbonylfortimicin B (1), 8 ml of 37% aqueous formaldehyde, and 400 ml of methanol is allowed to stand overnight at room temperature. The major portion of the solvent is evaporated under reduced pressure. Residual water is removed by co-distillation with benzene leaving 16.3 g of the desired product as a white glass:NMR (CDCl$_3$ δ1.17d (J=6.5 Hz) (C$_{6'}$—CH$_3$), 2.28 (NCH$_3$), 2.80q (J$_{3,4}$=6.5 Hz, J$_{4,5}$=2.0 Hz) (C$_4$—H); 3.5 (OCH$_3$); 3.81d, 4.60d (OCH$_2$—N) (J=2.3 Hz).

We claim:

1. A 1,2-carbamate of fortimicin B and derivatives represented by the formula

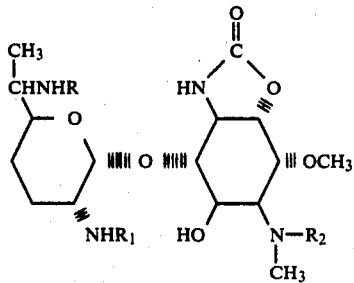

wherein: R is hydrogen or a monocyclicaryloxycarbonyl amine-protecting group; $R_1$ is hydrogen or a monocyclicaryloxycarbonyl amine-protecting group; and $R_2$ is selected from the group consisting of loweralkyl, loweralkoxycarbonyl, aminoloweralkyl, hydroxyloweralkyl, hydroxy-substituted aminoloweralkyl, an amino acid residue, an N-protected amino acid residue, and when R or $R_1$ are hydrogen, $R_2$ can also be hydrogen, and when any of R, $R_1$ or $R_2$ are hydrogen, the acid addition salts thereof.

2. A compound of claim 1 wherein $R_2$ is loweralkyl.
3. A compound of claim 2 wherein R and $R_1$ each are a monocyclicaryloxycarbonyl amine-protecting group.
4. A compound of claim 2 wherein R and $R_1$ each are hydrogen.
5. A compound of claim 1 wherein $R_2$ is loweralkoxycarbonyl.
6. A compound of claim 5 wherein R and $R_1$ each are hydrogen.
7. A compound of claim 5 wherein R and $R_1$ each are a monocyclicaryloxycarbonyl amine-protecting group.
8. 4-N-ethoxycarbonyl-2'6'-di-N-benzyloxycarbonyl-fortimicin B-1,2-carbamate.
9. 4-N-Methyl-2'6'-di-N-benzyloxycarbonylfortimicin B-1,2-carbamate.
10. Fortimicin B-1,2-carbamate or a salt thereof.
11. A compound of claim 10, fortimicin B-1,2-carbamate trihydrochloride.
12. 4-N-Methylfortimicin B-1,2-carbamate or a salt thereof.
13. A compound of claim 12, 4-N-methylfortimicin B-1,2-carbamate trihydrochloride.

* * * * *